United States Patent
Scheibel

(10) Patent No.: US 10,561,723 B2
(45) Date of Patent: Feb. 18, 2020

(54) TREATMENT AND PREVENTION OF ANAL CONDITIONS

(71) Applicant: Steven Frederick Scheibel, Palm Springs, CA (US)

(72) Inventor: Steven Frederick Scheibel, Palm Springs, CA (US)

(73) Assignee: Theodore C. Marbley, Palm Springs, CA (US)

(*) Notice: Subject to any disclaimer, the term of this patent is extended or adjusted under 35 U.S.C. 154(b) by 0 days.

(21) Appl. No.: 15/743,133

(22) PCT Filed: Jul. 21, 2016

(86) PCT No.: PCT/US2016/043419
§ 371 (c)(1),
(2) Date: Jan. 9, 2018

(87) PCT Pub. No.: WO2017/015504
PCT Pub. Date: Jan. 26, 2017

(65) Prior Publication Data
US 2019/0105384 A1   Apr. 11, 2019

Related U.S. Application Data

(60) Provisional application No. 62/194,941, filed on Jul. 21, 2015.

(51) Int. Cl.
*A61K 39/12* (2006.01)
*C07K 16/28* (2006.01)
*C07K 16/46* (2006.01)
*A61P 31/20* (2006.01)
*A61P 35/00* (2006.01)
*A61K 31/4745* (2006.01)
*A61K 9/00* (2006.01)
*A61K 31/519* (2006.01)
*A61K 31/7064* (2006.01)
*A61K 39/395* (2006.01)
*A61K 39/42* (2006.01)
*C07K 16/08* (2006.01)
*A61K 39/00* (2006.01)

(52) U.S. Cl.
CPC ............ *A61K 39/12* (2013.01); *A61K 9/0031* (2013.01); *A61K 31/4745* (2013.01); *A61K 31/519* (2013.01); *A61K 31/7064* (2013.01); *A61K 39/39558* (2013.01); *A61K 39/42* (2013.01); *A61P 31/20* (2018.01); *A61P 35/00* (2018.01); *C07K 16/084* (2013.01); *C07K 16/28* (2013.01); *C07K 16/46* (2013.01); *A61K 2039/545* (2013.01); *A61K 2039/55* (2013.01)

(58) Field of Classification Search
None
See application file for complete search history.

(56) References Cited

U.S. PATENT DOCUMENTS

| 7,410,758 B2 | 8/2008 | Sastry et al. |
| 8,426,387 B2 | 4/2013 | Carper et al. |
| 2009/0060870 A1* | 3/2009 | van der Burg ..... A61K 31/4745 514/1.1 |

FOREIGN PATENT DOCUMENTS

| CN | 103772508 A | 5/2014 |
| EP | 1002110 B2 | 5/2000 |
| WO | 2015095811 A2 | 6/2015 |
| WO | 2015106281 A1 | 7/2015 |
| WO | 2016139362 A1 | 9/2016 |
| WO | 2017015504 A1 | 1/2017 |

OTHER PUBLICATIONS

Chuang et al. Treatment with Imiquimod enhances antitumor immunity induced by therapeutic HPV DNA vaccination. Journal of Biomedical Science, 2010, 17:32.*
Daayana et al. Phase II trial of imiquimod and HPV therapeutic vaccination in patients with vulval intraepithelial neoplasia. British Journal of Cancer (2010) 102, 1129-1136.*
Lee et al. Condyloma accuminatum treated with recombinant quadrivalent human papillomavirus vaccine (types 6, 11, 16, 18). J Am Acad Dermatol. Jun. 2011;64(6):e130-2.*
Gemigniani et al. Focal epithelial hyperplasia by human papillomavirus (HPV)-32 misdiagnosed as HPV-16 and treated with combination of retinoids, imiquimod and quadrivalent HPV vaccine. Journal of Dermatology 2015; 42: 1172-1175.*
Wieland et al. Imiquimod Treatment of Anal Intraepithelial Neoplasia in HIV-Positive Men. Arch Dermatol. 2006;142:1438-1444.*
Palefsky et al. A trial of SGN-00101 (HspE7) to treat high-grade anal intraepithelial neoplasia in HIV-positive individuals. AIDS 2006, 20:1151-1155.*
Weis, SE. Current treatment options for management of anal intraepithelial neoplasia OncoTargets and Therapy 2013:6 651-665.*
Palefsky et al. HPV Vaccine against Anal HPV Infection and Anal Intraepithelial Neoplasia. N Engl J Med 2011;365:1576-85.*
International Search Report and Written Opinion for PCT/US2016/43419 dated Oct. 18, 2016, 12 pages.
International Preliminary Report on Patentability for PCT/US2016/43419 dated Jan. 23, 2018, 11 pages.
Bhardwaj et al., TLR Agonists: Are They Good Adjuvants?, Cancer Journal, 2010, vol. 16(4), pp. 382-391.
3M Health Care Limited, Aldara® (imiquimod) Cream Full Prescribing Information, 2010, retrieved from: [https://accessdata.fda.gov/drugsatfda_docs/label/2010/020723s022lbl.pdf] on Sep. 23, 2016.

(Continued)

Primary Examiner — Nianxiang Zou
(74) Attorney, Agent, or Firm — Nixon Peabody LLP

(57) ABSTRACT

The invention relates to methods, compositions, and kits for treating a condition with an immune response modifier and a human papillomavirus (HPV) vaccine. Conditions treatable with the methods, kits and compositions include but are not limited to neoplasia, anal intraepithelial neoplasia, high-grade squamous intraepithelial neoplasia, dysplasia, anal dysplasia, dysplastic lesion, high-grade dysplastic lesion, condyloma, anal cancer, anal tumor, HPV infection, and any HPV-induced condition.

36 Claims, 5 Drawing Sheets

(56) References Cited

OTHER PUBLICATIONS

Medscape, Nitroglycerine Rectal (RX)—Reactiv. Datasheet, 2014, retrieved from: [http://reference.medscape.com/drug/rectiv-nitroglycerin-rectal-999667] on Sep. 26, 2016.

* cited by examiner

TREATMENT AND PREVENTION OF ANAL CONDITIONS

CROSS-REFERENCE TO RELATED APPLICATION

This application is a National Phase of International Application No. PCT/US2016/43419, filed Jul. 21, 2016, which designated the U.S. and that International Application was published under PCT Article 21(2) in English. This application claims the benefit under 35 U.S.C. § 119(e) of U.S. Provisional Patent Application No. 62/194,941 filed on Jul. 21, 2015, which is incorporated herein by reference in its entirety.

FIELD OF THE INVENTION

The present invention relates to the field of medicine and the treatment and prevention of viral infections and anal conditions.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The rates of anal cancer among men who have sex with men (MSM) have been increasing, especially in HIV positive MSM, and are currently 80 times the rate of the general population. To screen for anal cancer and anal dysplasia both HIV infected and uninfected MSM receive a digital anal rectal examination (DARE) as well as an anal pap smear. An abnormal anal pap smear or the presence of high-risk oncogenic human papilloma virus (HPV), indicate the need for high resolution anoscopy (HRA) with biopsy. High-grade squamous intraepithelial neoplasia is a precursor lesion to anal cancer and treated with ablative, topical or surgical treatments. However, the current standard of care results in a greater than 50% reoccurrence of dysplasia. This necessitates repeated anoscopic examinations with biopsies and various ablative, topical or surgical approaches to treat these high-grade dysplastic lesions, which is unacceptable to many patients because of repeated painful examinations, biopsies and treatments. Furthermore, ablative treatments do not provide protections from the re-emergence dysplasia or HPV DNA, either through reactivation of latent HPV or acquisition of new strains of HPV DNA.

There is clearly a need in the art for improved compositions, methods, and kits for treating and preventing anal cancer and related conditions.

SUMMARY OF THE INVENTION

In various embodiments, the invention teaches a method for treating a condition in a subject, comprising: providing an immune response modifier and a human papillomavirus (HPV) vaccine; and administering a therapeutically effective amount of the immune response modifier and the HPV vaccine to the subject, thereby treating the condition in the subject. In some embodiments, the condition is selected from the group consisting of neoplasia, anal intraepithelial neoplasia, high-grade squamous intraepithelial neoplasia, dysplasia, anal dysplasia, dysplastic lesion, high-grade dysplastic lesion, condyloma, anal cancer, anal tumor, HPV infection, an HPV-induced condition, and combinations thereof. In certain embodiments, the HPV-induced condition is neoplasia, anal intraepithelial neoplasia, high-grade squamous intraepithelial neoplasia, dysplasia, anal dysplasia, dysplastic lesion, high-grade dysplastic lesion, condyloma, anal cancer, or anal tumor. In some embodiments, the subject is a human. In certain embodiments, the subject is a male human. In certain embodiments, the subject is a female human. In some embodiments, the immune response modifier and the HPV vaccine are provided in one composition. In certain embodiments, the immune response modifier and the HPV vaccine are provided in separate compositions. In some embodiments, the immune response modifier and the HPV vaccine are administered concurrently, sequentially, or alternatively. In certain embodiments, the immune response modifier and the HPV vaccine are administered according to different schedules. In some embodiments, the immune response modifier is administered before, during or after administering the HPV vaccine. In certain embodiments, the immune response modifier is an immunostimulant. In some embodiments, the immune response modifier is a local immunostimulant. In certain embodiments, the immune response modifier is a toll-like receptor 7 (TLR7) agonist. In some embodiments, the immune response modifier is selected from the group consisting of: imiquimod, resiquimod, ANA975 (Isotorabine), ANA773, IPH-32XX, R848, CL097, 852A, CROI2015, GS-9620, PF-4878691, PF-4878691, and a combination thereof. In certain embodiments, the immune response modifier is administered intraanally. In some embodiments, the immune response modifier is administered at a dose of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg.

In certain embodiments, the immune response modifier is administered at a dose of about 0.001 0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$. In some embodiments, the immune response modifier is administered at about 1-10, 10-20, 20-30, 30-40, 40-50, 50-60, 60-70, 70-80, 80-90, or 90-100 mg per dose. In certain embodiments, the immune response modifier is administered about 1-3 times per day, 1-7 times per week, 1-9 times per month, or 1-12 times per year. In some embodiments, the immune response modifier is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In certain embodiments, the HPV vaccine is a nonavalent HPV vaccine, bivalent HPV vaccine, quadrivalent HPV vaccine, or 9-valent HPV vaccine, or a combination thereof. In some embodiments, the HPV vaccine is Gardasil, Gardasil 4, Gardasil 9, or Cervarix, or a combination thereof. In certain embodiments, the HPV vaccine is a vaccine protective against HPV 6, 11, 40, 42, 43, 44, 53, 54, 61, 72, 73, 81, 16, 18, 31, 33, 35, 39, 45, 51, 52, 56, 58, 59, or 68, or a combination thereof. In some embodiments, the HPV vaccine is administered intramuscularly, or perianally, or a combination thereof. In certain embodiments, the HPV vaccine is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg. In certain embodiments, the immune response modifier is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$. In certain embodiments, the HPV vaccine is administered about 1-3 times per day, 1-7 times per week, 1-9 times per month, or 1-12 times per year. In some embodiments, the HPV vaccine is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In certain embodiments, a first dose of the immune response modifier and a first dose of the HPV vaccine are administered concurrently. In some embodiments, the immune response modifier is administered intra-anally. In certain embodiments, the immune response modifier is administered once every about two days. In some embodiments, the immune response modifier is administered about three times per week. In certain embodiments, a first dose of the HPV vaccine is administered intramuscularly. In some embodiments, a second dose of the HPV vaccine is administered perianally. In certain embodiments, the HPV vaccine is administered once every about three weeks. In certain embodiments, the immune response modifier and the HPV vaccine are administered for about 1-5, 5-10, 10-15, 15-20, 20-25, 25-30, 30-35, 35-40, 40-45, or 45-50 weeks.

In various embodiments, the invention teaches a composition comprising an immune response modifier and an HPV vaccine.

In various embodiments, the invention teaches a kit for treating the progression of a condition in a subject, comprising: a quantity of an immune response modifier; a quantity of an HPV vaccine; and instructions for using the immune response modifier and the HPV vaccine to treat the condition in the subject.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1A:
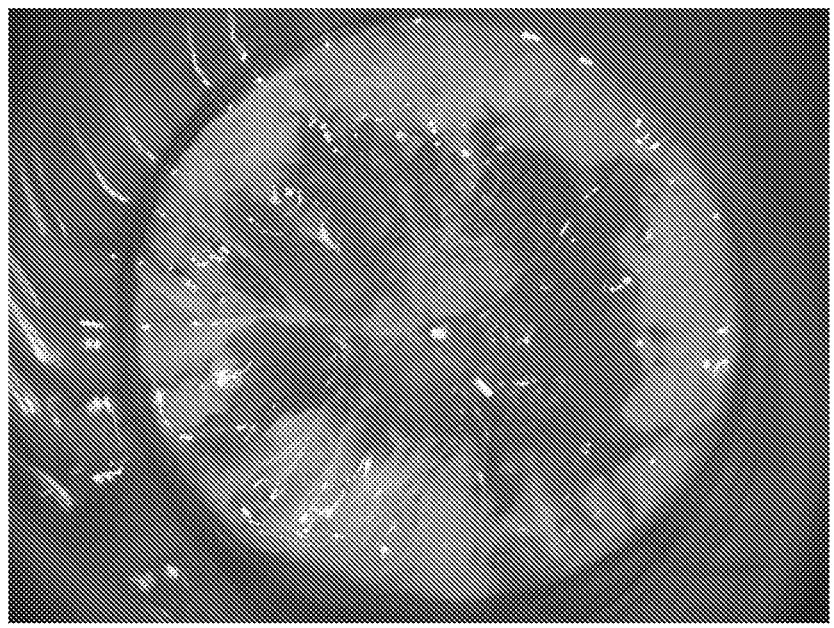
FIG. 1A depicts, in accordance with various embodiments of the invention, transition zone of anal canal on Nov. 6, 2014 at initial HRA exam with 5% acetic acid.

All references cited herein are incorporated by reference in their entirety as though fully set forth. Unless defined otherwise, technical and scientific terms used herein have the same mea ning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Kohler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of HPV infection, delay or slowing of HPV infection, and amelioration or palliation of symptoms associated with HPV infection.

"Disorders", diseases", "conditions" and "disease conditions," as used herein may include, but are in no way limited to any form of HPV infection and HPV-induced disorders, diseases or conditions. Examples include but are not limited to neoplasia, anal intraepithelial neoplasia, high-grade squamous intraepithelial neoplasia, dysplasia, anal dysplasia, dysplastic lesion, high-grade dysplastic lesion, condyloma, anal cancer, and anal tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant tumors, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. As used herein, the term "carcinoma" refers to a cancer arising from epithelial cells.

Unless indicated otherwise by specific context, as used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein. In various embodiments, a method as disclosed herein utilizes the intra-anal and/or perianal route of administration.

The term "sample" or "biological sample" as used herein denotes a sample taken or isolated from a biological organism, e.g., a tumor sample from a subject. Exemplary biological samples include, but are not limited to, cheek swab, anal swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. The animal may be a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. The methods described herein can also be used to treat animals with immune systems that have been modified to resemble the immune system of a human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., HPV infection) or one or more complications related to the condition, and optionally has already undergone treatment for the condition or the one or more complications related to the condition. Alternatively, a subject can be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

By way of additional background and context, the incidence of anal cancer in USA has been increasing in the general population from 1.2/100,000 cases in 1992 to about 1.8/100,000 estimated in 2014. The incidence of anal cancer is increased in HIV positive men who have sex with men (MSMs). It has been estimated that the incidence of anal cancer among HIV-negative men who engaged in receptive anal intercourse (RAI) was up to 35/100,000. In 2012 the incidence of anal cancer among HIV infected MSM in North America was 131/100, 000. Therefore, as indicated above, HIV infection in MSM increases the risk of anal cancer by approximately 80 times that of the general population. HPV infection with oncogenic strains is associated with the emergence anal intraepithelial lesions (AIN), which is a grading system for dysplasia identical to cervical intraepithelial neoplasia (CIN). High grade squamous intraepithelial lesions (HSIL) or AIN 2 and AIN 3 are presumed to be the precursor lesions of anal squamous cell carcinoma. This is supported by a study from UCSF demonstrating the progression of HSIL to anal cancer, showing that 20/27 men progressed to anal cancer from prevalent HSIL lesions, providing evidence of the malignant potential of HSIL lesions. Prevention of anal cancer is dependent upon screening with anal pap smears for cytology and detection of oncogenic strains of HPV. The prevalence of abnormal anal pap cytology ranges from about 43-63% among MSMs with HIV disease. Additionally, HRA often reveals that the anal cytology under-predicted the occurrence of AIN when compared to pathology of biopsy specimens. In a large series of patients treated with HRA and ablative therapies followed at Stanford, there was a 57% recurrence rate at an average of 19 months. Therefore, HRA requires on-going frequent monitoring and ablative treatments of HSIL to prevent progression to squamous cell carcinoma.

Patients with abnormal anal pap smear results atypical squamous cells of uncertain significance (ASCUS or greater) undergo high resolution anoscopy (HRA), which is used to stain and identify abnormal tissue for biopsy. AIN 2 and AIN 3 lesions are treated with ablative therapies (hyfrecation, infrared coagulation, trichloroacetic acid) or surgical approaches using HRA guided $CO_2$ laser or excision, followed by periodic HRAs to monitor and treat recurrent high grade anal dysplasia. The effectiveness of topical or ablative treatment versus close observation in preventing the development of anal squamous carcinoma is being investigated in a US trial aimed at enrolling approximately 5000 patients. A clinical trial in Australia among homosexual men demonstrated regression of HSIL lesions with observation over three years; however, lesions representing high risk types (16, 18 and other high risk types) were not associated with spontaneous regression of anal high-grade squamous intraepithelial lesions (HSIL) in HIV positive and HIV negative homosexual patients. Thus, the effectiveness and durability of topical and ablative treatments for anal HSIL is considered unknown and currently being investigated.

Immunization is one approach to theoretically control the replication of HPV and possibly therefore treat the associated dysplastic lesions. The quadrivalent HPV vaccine has been tested in HIV positive men and found to be both immunogenic and safe. Therapeutic immunization with quadrivalent HPV vaccine (qHPV), is associated with a decreased risk of recurrent HSIL after 2 years in HIV negative MSMs. Immunizations reported were given IM in the deltoid region. Therefore, there is precedence in the use of qHPV vaccine associated with a decreased incidence of subsequent HSIL. Recently, nonavalent HPV vaccine (nHPV) has been available and is used to replace the qHPV vaccine with the presence of additional oncogenic strains of HPV. Gardasil-9 is not approved for the treatment of either AIN or CIN.

Imiquimod is a local immunostimulant, acting as a toll like receptor (TLC)-7 agonist, causing an increase in the local production of alpha-interferon and the recruitment of NK and B cells. This immunostimulant has been used in the treatment of actinic keratosis, superficial basal cell carcinomas and external genital warts. Intra-anal application of 5% imiquimod cream three times weekly for 16 weeks in 19 HIV positive men with AIN resulted in decreased HPV DNA viral loads and histologic clearance in 17/22 patients at the completion of therapy; however, long-term HPV clearance was rare, 5 patient developed recurrent AIN often associated with HPV types that differed from the start of the study. Thus, intra-anal imiquimod treatment is associated with loss of HPV DNA and normalization of histology, however, these beneficial effects are not sustained with either re-activation of latent HPV infection or the acquisition of new oncogenic types of HPV observed during a mean follow up time of approximately 30 months.

With the foregoing background in mind, various embodiments of the present invention result in a local HPV-specific immune response through perianal immunizations with a vaccine against HPV and/or intra-anal imiquimod (Systematic IUPAC name: 3-(2-Methylpropyl)-3,5,8-triazatricyclo [$7.4.0.0^{2,6}$]trideca-1(9),2(6),4,7,10,12-hexaen-7-amine; CAS Registry Number: 99011-02-6) cream to treat anal dysplasia as well as the underlying infection with HPV. In various embodiments, therapies disclosed herein result in a local HPV-specific immune response through perianal immunizations with GARDASIL (4 or 9) when used separately from or concurrently with intra-anal imiquimod cream to treat anal dysplasia as well as the underlying infection with HPV. In various embodiments, therapies disclosed herein can lead to clearance, eradication, or improvement of human papilloma virus (HPV) infection and resolution of anal dysplasia. There can also be immunologic protection against re-activation of HPV infection in the anal canal as well as protection against re-infection from sexual contact. Similar combination therapeutic approaches in non-human animals infected with viruses that behave similarly to HPV, in that they lead to similar pathologies, are also within the scope of the present invention.

In some embodiments, the present invention includes a therapy in which HPV vaccine (e.g. GARDASIL) is administered in conjunction with intra-anal imiquimod to produce a local enhanced cell mediated response against HPV. This differs from typical treatments which are ablative, surgical or chemotherapeutic and have significant morbidity and are associated with the high rates of recurrent anal dysplasia. In various embodiments, the therapies disclosed herein provide sustained immunologic protection against reactivation of HPV infection in the anal canal and protection against re-infection with ongoing sexual activity, avoids morbidity secondary to ablative therapy and/or surgery, and reduces the need for HRA (high resolution anoscopy) monitoring.

Some advantages of various embodiments of therapies disclosed herein include one or more of: 1) definitive treatment of anal dysplasia with little or no morbidity; 2) subsequent improved protection against the development of anal cancer; 3) reduction in the new acquisition of HPV strains as well as suppression of re-activation of latent HPV.

Treatment Methods

In various embodiments, the present invention provides a method for treating, preventing, reducing the likelihood of having, reducing the severity of and/or slowing the progression of a condition in a subject. The method may consist of or may consist essentially of or may comprise: providing an immune response modifier and a human papillomavirus (HPV) vaccine; and administering a therapeutically effective amount of the immune response modifier and the HPV vaccine to the subject, thereby treating, preventing, reducing the likelihood of having, reducing the severity of and/or slowing the progression of the condition in the subject.

In various embodiments, the condition is neoplasia, anal intraepithelial neoplasia, high-grade squamous intraepithelial neoplasia, dysplasia, anal dysplasia, dysplastic lesion, high-grade dysplastic lesion, condyloma, anal cancer, anal tumor, HPV infection, or an HPV-induced condition. In some embodiments, the HPV-induced condition is neoplasia, anal intraepithelial neoplasia, high-grade squamous intraepithelial neoplasia, dysplasia, anal dysplasia, dysplastic lesion, high-grade dysplastic lesion, condyloma, anal cancer, or anal tumor.

In various embodiments, the subject is a human. In some embodiments, the subject is a male human. In other embodiments, the subject is a female human. In various embodiments, the subject is a mammalian subject including but not limited to human, monkey, ape, dog, cat, cow, horse, goat, pig, rabbit, mouse and rat. In some embodiments, the subject has been infected with a virus with similar characteristics to HPV, but specific to non-humans.

In some embodiments, the immune response modifier and the HPV vaccine are provided in one composition. In other embodiments, the immune response modifier and the HPV vaccine are provided in separate compositions.

In various embodiments, the immune response modifier and the HPV vaccine are administered concurrently, sequentially, or alternatively. In various embodiments, the immune response modifier and the HPV vaccine are administered according to different schedules. In various embodiments, the immune response modifier is administered before, during or after administering the HPV vaccine.

In various embodiments, the immune response modifier is an immunostimulant. In some embodiments, the immune response modifier is a local immunostimulant. In some embodiments, the immune response modifier is a systemic immunostimulant. As used herein, "immunostimulants" and "immunostimulators" refer to substances (drugs and nutrients) that stimulate the immune system by inducing activation or increasing activity of any of its components.

In various embodiments, the immune response modifier is a toll-like receptor 7 (TLR7) agonist. Examples of TLR7 agonists include but are not limited to imiquimod, resiquimod, ANA975 (Isotorabine), ANA773, IPH-32XX, R848, CL097, 852A, CROI2015, GS-9620, PF-4878691, PF-4878691, and their functional equivalents, analogs, derivatives, variants and salts, and their combinations.

In various embodiments, the HPV vaccine is a nonavalent HPV vaccine, bivalent HPV vaccine, quadrivalent HPV vaccine, or 9-valent HPV vaccine, or a combination thereof. In various embodiments, the HPV vaccine is GARDASIL, GARDASIL 4, GARDASIL 9, or CERVARIX, or a combination thereof. In various embodiments, the HPV vaccine is a vaccine protective against HPV 6, 11, 40, 42, 43, 44, 53, 54, 61, 72, 73, 81, 16, 18, 31, 33, 35, 39, 45, 51, 52, 56, 58, 59, or 68, or a combination thereof.

In accordance with the invention, the immune response modifier and the HPV vaccine may be administered using the appropriate modes of administration, for instance, the modes of administration recommended by the manufacturer for each of the immune response modifier and the HPV vaccine. In accordance with the invention, various routes may be utilized to administer the immune response modifier and/or the HPV vaccine of the methods herein, including but not limited to intra-anal, perianal, intratumoral, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the immune response modifier and/or the HPV vaccine are administered intra-anally, perianally, intracranially, intraventricularly, intrathecally, epidurally, intradurally, topically, intravascularly, intravenously, intraarterially, intratumorally, intramuscularly, subcutaneously, intraperitoneally, intranasally, or orally. In some embodiments, the immune response modifier and the HPV vaccine may be administered via the same route. In other embodiments, the immune response modifier and the HPV vaccine may be administered via different routes. In certain embodiments, the immune response modifier is administered intra-anally. In certain embodiments, the HPV vaccine is administered intramuscularly, or perianally, or a combination thereof.

Typical dosages of an effective amount of the immune response modifier and/or the HPV vaccine and/or 5-fluorouracil (as indicated below) can be in the ranges recommended by the manufacturer where known therapeutic molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the immune response modifier and/or the HPV vaccine and/or 5-fluorouracil (as indicated below) may be administered once a day (SID/QD), twice a day (BID), three times a day (TID), four times a day (QID), or more, so as to administer an effective amount of the immune response modifier and/or the HPV vaccine and/or 5-fluorouracil (as indicated below) to the subject, where the effective amount is any one or more of the doses described herein.

In various embodiments, the method of treating, preventing, reducing the likelihood of having, reducing the severity of and/or slowing the progression of a condition described above includes administering (and optionally providing) 5-fluorouracil before, during, and/or after (or any combination of before, during, and after) administration of the immune response modifier and/or the HPV vaccine. In some embodiments, the 5-fluorouracil is administered peri-anally or intra-anally. In some embodiments, the 5-fluorouracil is administered in the form of a cream. In some embodiments, the 5-fluorouracil is administered intra-anally or peri-anally in the form of a cream before, during, and/or after (or any combination of before, during, and after) administration of an HPV vaccine and/or an immune response modifier. In some embodiments, the 5-fluorouracil is 1-20, 2-15, 3-10, or 5-8% w/v.

In various embodiments, the effective amount of the immune response modifier and/or the HPV vaccine and/or the 5-fluorouracil is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of the immune response modifier and/or the HPV vaccine and/or the 5-fluorouracil is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m$^2$/day, or a combination thereof. In various embodiments, the effective amount of the immune response modifier and/or the HPV vaccine and/or 5-fluorouracil is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the immune response modifier and/or the HPV vaccine and/or 5-fluorouracil is any one or more of about 0.001-0.01, 0.01-0.1, 0.1-0.5, 0.5-5, 5-10, 10-20, 50-100, 100-200, 200-300, 300-400, 400-500, 500-600, 600-700, 700-800, 800-900, or 900-1000 mg/m$^2$/day, or a combination thereof. Here, "µg/kg/day" or "mg/kg/day" refers to µg or mg per kg body weight of the subject per day, and "µg/m$^2$/day" or "mg/m$^2$/day" refers to µg or mg per m$^2$ body surface area of the subject per day.

In some embodiments, the immune response modifier and/or 5-fluorouracil is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the immune response modifier and/or 5-fluorouracil is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$, or a combination thereof. In certain embodiments, the immune response modifier and/or 5-fluorouracil is administered at about 1-10, 10-20, 20-30, 30-40, 40-50, 50-60, 60-70, 70-80, 80-90, or 90-100 mg per dose.

In various embodiments, the immune response modifier and/or 5-fluorouracil are administered once, twice, three or more times. In some embodiments, the immune response modifier and/or 5-fluorouracil are administered 1-3 times per day, 1-7 times per week, 1-9 times per month, or 1-12 times per year. In some embodiments, the immune response modifier and/or 5-fluorouracil is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject, and "mg/m$^2$" refers to mg per m$^2$ body surface area of the subject. In certain embodiments, the immune response modifier and/or 5-fluorouracil are administered to a human.

In some embodiments, the HPV vaccine is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In other embodiments, the HPV vaccine is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$, or a combination thereof.

In various embodiments, the HPV vaccine is administered once, twice, three or more times. In some embodiments, the HPV vaccine is administered 1-3 times per day, 1-7 times per week, 1-9 times per month, or 1-12 times per year. Still in some embodiments, the HPV vaccine is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject, and "mg/m$^2$" refers to mg per m$^2$ body surface area of the subject. In certain embodiments, the HPV vaccine is administered to a human.

In various embodiments, the immune response modifier's first dose and the HPV vaccine's first dose are administered concurrently. In various embodiments, the immune response modifier's doses are administered intra-anally. In various embodiments, the immune response modifier is administered once every about two days. In various embodiments, the immune response modifier is administered about three times per week. In various embodiments, the HPV vaccine's first dose is administered intramuscularly. In various embodiments, the HPV vaccine's second and later doses are administered perianally. In various embodiments, the HPV vaccine is administered once every about three weeks. In various embodiments, the immune response modifier and the HPV vaccine are administered for about 1-5, 5-10, 10-15, 15-20, 20-25, 25-30, 30-35, 35-40, 40-45, or 45-50 weeks. In various embodiments, when 5-fluorouracil (of any concentration described herein) is administered before, during, and/or after (or any combination of before, during, and after) administering the immune response modifier and/or the HPV vaccine, the 5-fluorouracil is administered for about 1-5, 5-10, 10-15, 15-20, 20-25, 25-30, 30-35, 35-40, 40-45, or 45-50 weeks at any dosage range described herein and with any dosage frequency (e.g. once a day, once a week, etc.) described herein.

In some embodiments, the immune response modifier and/or the HPV vaccine and/or 5-fluorouracil may be administered at the prevention stage of a condition (e.g., when the subject has not developed the condition but is likely to or in the process of developing the condition). In other embodiments, the immune response modifier and/or the HPV vaccine and/or 5-fluorouracil may be administered at the treatment stage of a condition (i.e., when the subject has already developed the condition). As a non-limiting example, the target condition is HPV infection. In some embodiments, the target condition is a condition associated with HPV and/or an anal condition described herein. In exemplar situations, the patient may be treated with the methods described herein when the patient has not yet developed HPV infection, or is likely to develop HPV infection, or is in the process of developing HPV infection, or has already developed HPV infection.

Pharmaceutical Compositions

In various embodiments, the present invention provides a composition that may consist of or may consist essentially of or may comprise one or more of an immune response modifier, an HPV vaccine, and 5-fluorouracil. In one embodiment, the composition may consist of or may consist essentially of or may comprise an immune response modifier and an HPV vaccine. In another embodiment, the composition may consist of or may consist essentially of or may comprise an immune response modifier. In still another embodiment, the composition may consist of or may consist essentially of or may comprise an HPV vaccine.

In accordance with the present invention, the compositions described herein may be used for treating, preventing, reducing the likelihood of having, reducing the severity of and/or slowing the progression of a condition in a subject. In various embodiments, the condition is neoplasia, anal intraepithelial neoplasia, high-grade squamous intraepithelial neoplasia, dysplasia, anal dysplasia, dysplastic lesion, high-grade dysplastic lesion, condyloma, anal cancer, anal tumor, HPV infection, an HPV-induced condition, or a combination of the foregoing conditions. In some embodiments, the HPV-induced condition is neoplasia, anal intraepithelial neoplasia, high-grade squamous intraepithelial neoplasia, dysplasia, anal dysplasia, dysplastic lesion, high-grade dysplastic lesion, condyloma, anal cancer, or anal tumor.

In various embodiments, the immune response modifier is a toll-like receptor 7 (TLR7) agonist. Examples of TLR7 agonists include but are not limited to imiquimod, resiquimod, ANA975 (Isotorabine), ANA773, IPH-32XX, R848, CL097, 852A, CROI2015, GS-9620, PF-4878691, PF-4878691, and their functional equivalents, analogs, derivatives, variants and salts, and their combinations. In an embodiment, the immune response modifier is imiquimod.

In various embodiments, the HPV vaccine is a nonavalent HPV vaccine, bivalent HPV vaccine, quadrivalent HPV vaccine, or 9-valent HPV vaccine, or a combination thereof. In various embodiments, the HPV vaccine is GARDASIL, GARDASIL 4, GARDASIL 9, or CERVARIX, or a combination thereof. In some embodiments, the HPV vaccine is a vaccine against HPV 6, 11, 40, 42, 43, 44, 53, 54, 61, 72, 73, 81, 16, 18, 31, 33, 35, 39, 45, 51, 52, 56, 58, 59, or 68, or a combination thereof.

In various embodiments, the immune response modifier and/or the 5-fluorouracil in the composition is provided in mg per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the immune response modifier and/or 5-fluorouracil in the composition is provided in mg per $m^2$ body surface area of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/$m^2$, or a combination thereof. In certain embodiments, the immune response modifier and/or 5-fluorouracil in the composition is provided about 1-10, 10-20, 20-30, 30-40, 40-50, 50-60, 60-70, 70-80, 80-90, or 90-100 mg per dose.

In various embodiments, the HPV vaccine in the composition is provided in mg per kilogram body weight of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the HPV vaccine in the composition is provided in mg per $m^2$ body surface area of the subject, for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/$m^2$, or a combination thereof.

In various embodiments, one or more of the compositions described herein can be formulated for intra-anal, perianal, intracranial, intraventricular, intrathecal, epidural, intradural, topical, intravascular, intravenous, intraarterial, intratumoral, intramuscular, subcutaneous, intraperitoneal, intranasal or oral administration. In some embodiments, a composition comprising an immune response modifier and/or 5-fluorouracil is formulated for intra-anal administration. In one embodiment, a composition comprising an HPV vaccine is formulated for intramuscular and perianal administration. In one embodiment, a composition comprising an HPV vaccine is formulated for intramuscular administration. In one embodiment, a composition comprising an HPV vaccine is formulated for perianal administration.

Preferred compositions will also exhibit minimal toxicity when administered to a mammal.

In various embodiments, the pharmaceutical compositions according to the invention may be formulated for delivery via any route of administration. "Route of administration" may refer to any administration pathway known in the art, including but not limited to intra-anal, perianal, aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art.

In various embodiments, any of the compositions described herein can be administered 1-3 times per day, 1-7 times per week, 1-9 times per month, or 1-12 times per year. In various embodiments, any of the compositions described herein can be administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, any of the compositions described herein can be administered once a day (SID/QD), twice a day (BID), three times a day (TID), four times a day (QID), or more, so as to administer an effective amount of the immune response modifier and/or the HPV vaccine and/or 5-fluorouracil to the subject, where the effective amount is any one or more of the doses described herein.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The pharmaceutical composition according to the invention can also be a bead system for delivering the therapeutic agent to the target cells. For example, pectin/zein hydrogel bead system may be used to deliver Neuregulin-4 or a pharmaceutical equivalent, analog, derivative or a salt thereof, to the target cells in the subject (Yan F. et al., J Clin Invest. 2011 June; 121(6):2242-53).

Kits

In various embodiments, the present invention provides a kit for treating, preventing, reducing the severity of and/or slowing the progression of a condition in a subject (e.g. any condition or combination of conditions described herein). The kit may consist of or may consist essentially of or may comprise: a quantity of an immune response modifier; a quantity of an HPV vaccine; and instructions for using the immune response modifier and the HPV vaccine to treat, prevent, reduce the likelihood of having, reduce the severity of and/or slow the progression of the condition in the subject. In various embodiments, the kit may consist of or consist essentially of or comprise one or more composition comprising one or more of a quantity of 5-fluorouracil, an immune response modifier, and an HPV vaccine described herein. In some embodiments, In various embodiments, the immune response modifier is a toll-like receptor 7 (TLR7) agonist. Examples of TLR7 agonists include but are not limited to imiquimod, resiquimod, ANA975 (Isotorabine), ANA773, IPH-32XX, R848, CL097, 852A, CROI2015, GS-9620, PF-4878691, PF-4878691, and their functional equivalents, analogs, derivatives, variants and salts, and their combinations.

In various embodiments, the HPV vaccine is a nonavalent HPV vaccine, bivalent HPV vaccine, quadrivalent HPV vaccine, or 9-valent HPV vaccine, or a combination thereof. In various embodiments, the HPV vaccine is GARDASIL, GARDASIL 4, GARDASIL 9, or CERVARIX, or a combination thereof. In various embodiments, the HPV vaccine is a vaccine protective against HPV 6, 11, 40, 42, 43, 44, 53, 54, 61, 72, 73, 81, 16, 18, 31, 33, 35, 39, 45, 51, 52, 56, 58, 59, or 68, or a combination thereof.

The kit is an assemblage of materials or components, including at least one of the inventive compositions or components. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the compositions or components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays and therapies. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following examples, which are intended to be purely exemplary of the invention, and should not be considered as limiting the invention in any way. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 Perianal Immunizations with Quadrivalent HPV Vaccine and Concurrent Imiquimod. Treating HPV and Anal Intraepithelial Neoplasia (AIN) in an HIV Negative Male As indicated above, the rates of anal cancer among MSM have been increasing, especially, in HIV positive MSM, with 80 times the rate of the general population. Treatment of anal dysplasia has been shown to prevent anal cancer. The following non-liming example describes the use of HPV4 vaccine in conjunction with imiquimod to treat anal dysplasia.

Case Report Summary: A 55 year old HIV negative male patient with multifocal AIN 2 and AIN 3 in the anal transitional zone was enrolled. The patient was treated with intra-anal imiquimod followed by an intramuscular dose of HPV4 followed by four perianal HPV4 immunizations, each separated by 3-4 weeks. The patient was screened for high risk (HR) HPV DNA on a weekly basis and had multiple biopsies to identify possible dysplasia.

Use of imiquimod in conjunction with successive perianal HPV4 immunizations resulted in the loss of HR HPV DNA including HPV16, normalization of the anal Pap smear from ASCUS, and resolution of anal dysplasia.

Use of intra-anal imiquimod in conjunction with perianal immunizations with HPV4 vaccine can result in regression of patients with AIN and loss of HR HPV DNA. Additionally, it is likely to reduce reactivation of latent HR HPV DNA and acquisition of novel oncogenic HPV through the generation of HPV specific immunity.

Figure 1B:
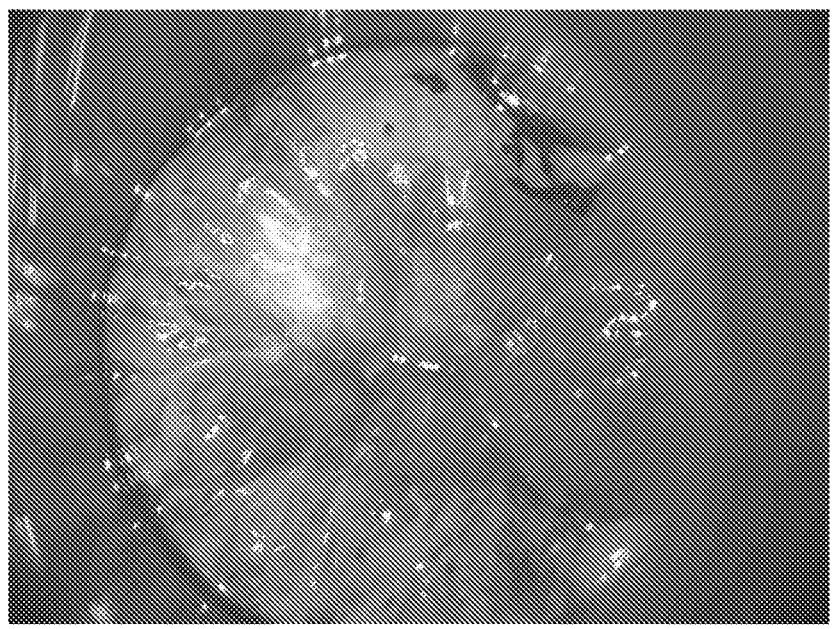
FIG. 1B depicts, in accordance with various embodiments of the invention, posterior view of transition zone on Nov. 6, 2014 with Lugol's iodine.
Figure 1C:
FIG. 1C depicts, in accordance with various embodiments of the invention, anterior view of transition zone on Nov. 6, 2014 with Lugol's iodine.

Detailed Data and Results: A 55 year old HIV negative male presented for routine health care. The results of a screening anal pap was positive for HPV 16 as well as other high risk HPV types and the cytology on the anal pap revealed atypical squamous cells of uncertain significance. Patient was referred for HRA. FIG. 1A shows an irregularly thick and acetowhite transitional zone on Nov. 5, 2014. Biopsies indicated the following: distal AIN 1 at three o'clock; AIN 1 at 4 o'clock; AIN 2 at 7 o'clock; AIN 2 at 10 o'clock; and AIN 2 at 12 o'clock. FIGS. 1B and 1C are posterior and anterior views, respectively, showing circumferential staining of the anal canal. Patient received the first immunization with qHPV vaccine IM in the deltoid on Nov. 13, 2014. On Dec. 1, 2014, the patient received the first perianal qHPV vaccine. He started to use 5% imiquimod on Dec. 1, 2014 with one packet applied intra-anally three times weekly.

The patient was seen again on Dec. 11, 2014 and had repeat HRA with biopsies indicting the following: AIN 1 at 4 o'clock; AIN 2 at 7 o'clock and AIN 3 at 12 o'clock. Patient received 0.5 cc qHPV vaccine in the perianal region for the second perianal immunization on Dec. 11, 2014. The anal pap was negative for high risk HPV DNA.

Figure 2A:
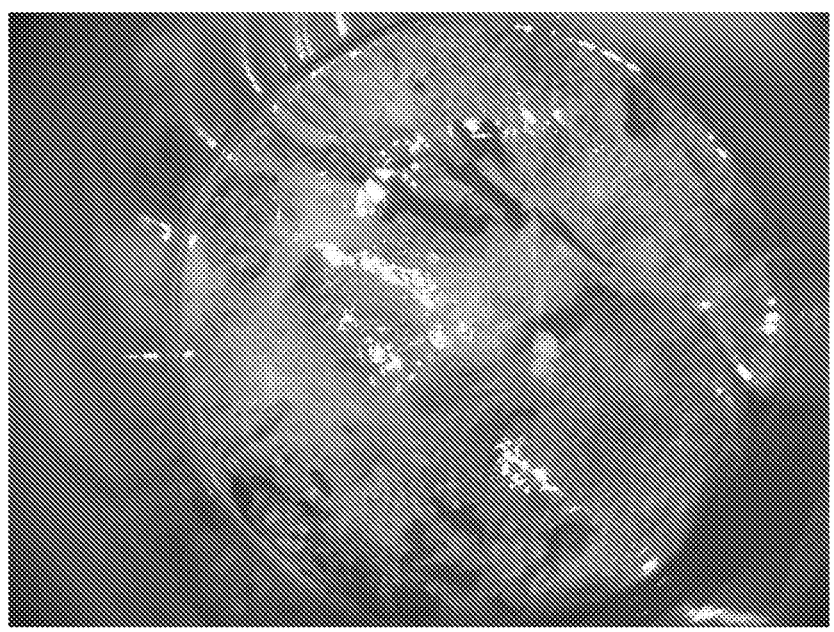
FIG. 2A depicts, in accordance with various embodiments of the invention, transition zone with acetowhite changes at week 7.
Figure 2B:
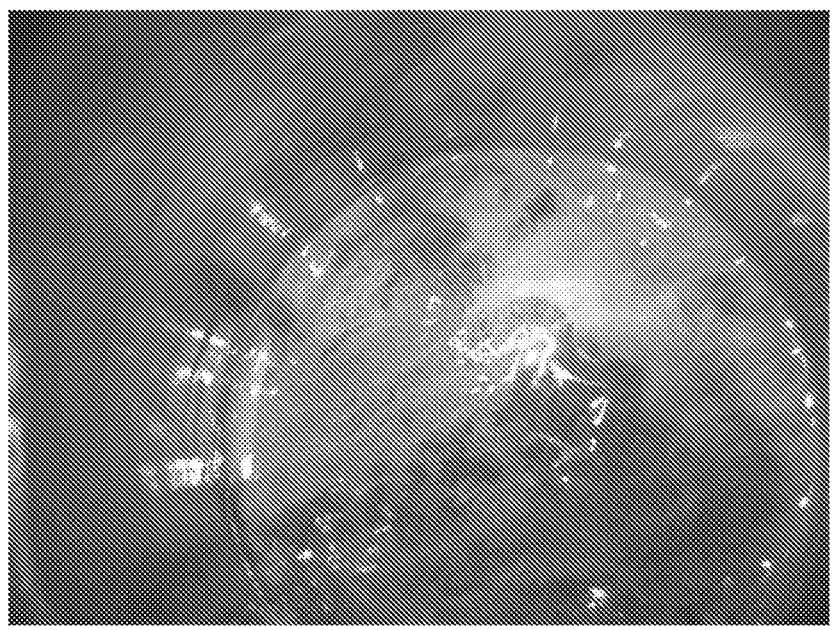
FIG. 2B depicts, in accordance with various embodiments of the invention, transition zone with acetowhite changes at week 7.

On Dec. 29, 2014 the patient was again examined and had ASCUS anal pap smear. The anal pap was negative for high risk HPV types. HRA with biopsies showed AIN 2 at 7 o'clock and focal AIN 1 at 12 o'clock. Patient continued with the imiquimod cream and had several interruptions due to the increased perianal erythema. See FIGS. 2A and 2B. The erythema and discomfort resolved and imiquimod was restarted after a period of several days to one week. On Jan. 27, 2015 the anal pap smear was normal and negative for high risk HPV DNA. He received the third perianal qHPV vaccine. Biopsies at 2, 6, 10 and 12 o'clock were all normal without evidence of dysplasia.

Figure 3A:
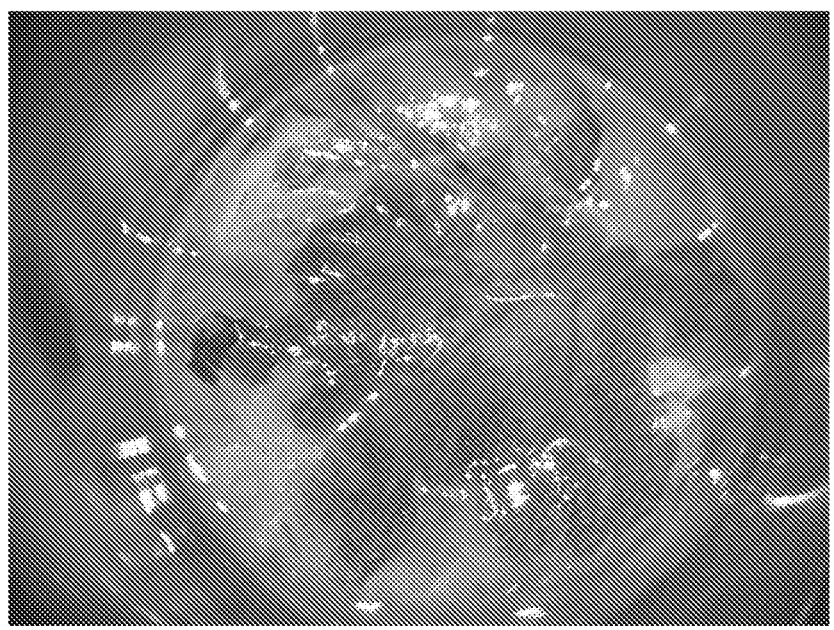
FIG. 3A depicts, in accordance with various embodiments of the invention, transition zone of anal canal on Feb. 15, 2015 with 5% acetic acid.
Figure 3B:
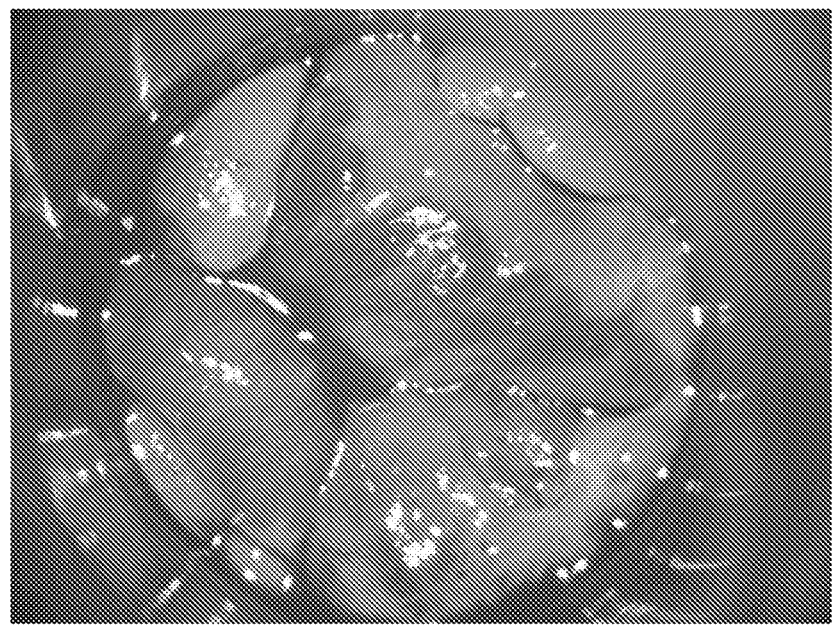
FIG. 3B depicts, in accordance with various embodiments of the invention, transition zone of anal canal on Feb. 15, 2015 with 5% acetic acid.
Figure 4A:
FIG. 4A depicts, in accordance with various embodiments of the invention, 5% acetic acid staining of the transitional zone showing thin translucent epitheilum with evidence of anorectal fissure 5 weeks after the end of treatment.
Figure 4B:
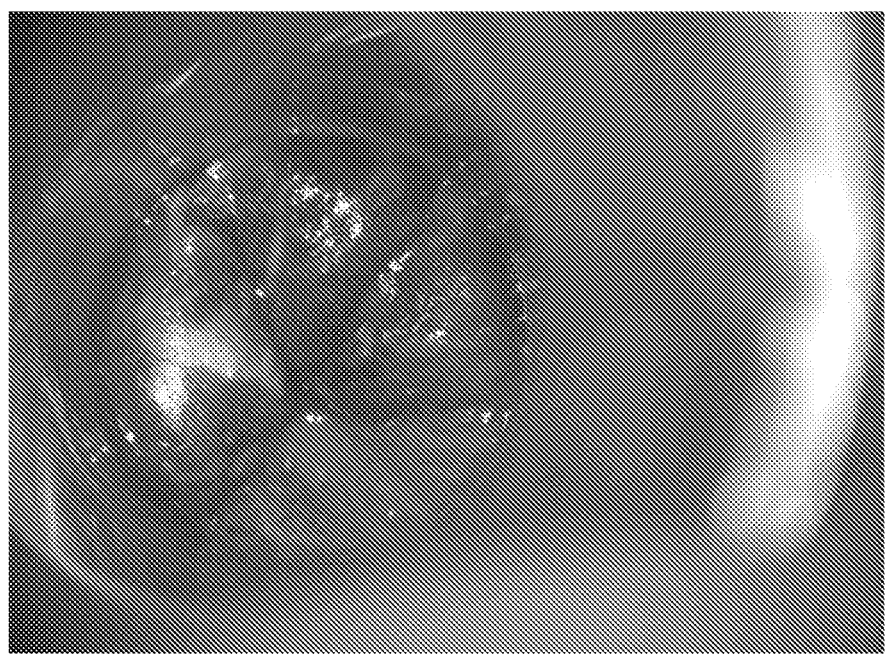
FIG. 4B depicts, in accordance with various embodiments of the invention, Lugol's counterstain with good uptake in the anal epithelium at the transitional zone. The vascular region represents anorectal fissure 5 weeks after end of treatment.

Patient was again seen on Feb. 10, 2015 and anal pap was normal and negative for high risk HPV DNA. HRA with biopsies showed at normal histology at 4, AIN 1 at 10 and small focal AIN 2 at 12 o'clock. See FIGS. 3A and 3B.

On Feb. 25, 2015, the patient had HRA with biopsies at 12, 5, 7 and 10 o'clock positions. Again, the anal pap smear is normal and HPV DNA is negative. He received the fourth perianal qHPV vaccine. Results of the biopsies are as follows.

Pathology Report I
Material Submitted:
Part A: anal canal, 4 o'clock (transition zone);
Part B: anal canal, 7 o'clock (transition zone);
Part C: anal canal, 10 o'clock (transition zone);
Part D: anal canal, 12 o'clock (transition zone).
Clinical History:
History of HSIL/status post: vaccine with aldare treatment;
Biopsy to rule out AIN 2/3;
Prior HSIL at 4, 7, 10, 12 o'clock.
Diagnosis:
A. anal canal, 4 o'clock (transition zone):
Anorectal junctional mucosa show marked reactive and repair changes.
There is no evidence of dysplasia or malignancy.
B. anal canal, 7 o'clock (transition zone):
Primarily blood and no viable tissue identified (tissue did not survive processing).
C. anal canal, 10 o'clock (transition zone):
Anal intraepithelial neoplasia, AIN 1, low-grade squamous intraepithelial lesion (LSIL).
D. anal canal, 12 o'clock (transition zone):
A focus of anal intraepithelial neoplasia, AIN 2, high-grade squamous intraepithelial lesion (HSIL).

Comment:

Concurrent pap (042-c45-4002-0) findings are negative for intraepithelial lesion and malignancy. Case was discussed with anoscopist and ANP (Adult Nurse Practitioner) on Feb. 18, 2015.

Pathology Report II
Material Submitted:
Part A: anal canal biopsy, 5 o'clock;
Part B: anal canal biopsy, 7 o'clock;
Part C: anal canal biopsy, 10 o'clock;
Part D: anal canal biopsy, 12 o'clock.
Clinical History:
History of AIN 2/3, under treatment.
Prior location of HSIL.
Most recent anal canal biopsies Feb. 11, 2015 (042-p75-0043-0).
Rule out HSIL.
Diagnosis:
A. anal canal biopsy, 5 o'clock:
Anal mucosa showing reactive cellular changes.
There is no evidence of dysplasia or malignancy.
B. anal canal biopsy, 7 o'clock:
Anal mucosa showing marked reactive cellular changes.
There is no evidence of dysplasia or malignancy.
C. anal canal biopsy, 10 o'clock:
Anal mucosa showing marked reactive cellular changes.
There is no evidence of dysplasia or malignancy.
D. anal canal biopsy, 12 o'clock:
Anorectal mucosa showing marked reactive cellular changes.
There is no evidence of dysplasia or malignancy.
Comment:
Concurrent thin prep anal pap sample is negative for intraepithelial lesion and malignancy. Intra-group consultation obtained.
Gross Description:
4 containers, formalin-filled, labeled with patient identification.
Part A: anal canal biopsy, 5 o'clock:
Received labeled "5 o'clock". The specimen consists of a single piece of tan-white tissue measuring 0.2×0.1×0.1 cm in greatest dimension. The specimen is wrapped and entirely submitted in 1 cassette(s).
Part B: anal canal biopsy, 7 o'clock:
Received labeled "7 o'clock". The specimen consists of a single piece of tan-white tissue measuring 0.2×0.2×0.1 cm in greatest dimension. The specimen is wrapped and entirely submitted in 1 cassette(s).
Part C: anal canal biopsy, 10 o'clock:
Received labeled "10 o'clock". The specimen consists of a single piece of tan-white tissue measuring 0.2×0.2×0.1 cm in greatest dimension. The specimen is wrapped and entirely submitted in 1 cassette(s).
Part D: anal canal biopsy, 12 o'clock:
Received labeled "12 o'clock". The specimen consists of multiple tan-white fragments of tissue, measuring 0.4×0.3×0.1 cm in aggregate dimension. The specimen is wrapped and entirely submitted in 1 cassette(s).

Results of the HPV DNA from Feb. 25, 2015 include: (1) the use of imiquimod in conjunction with successive perianal immunizations was associated initially with the loss of HPV DNA, followed by normalization of the anal pap smear and finally resolution of anal dysplasia in this case report of an HIV negative patient having circumferential high grade dysplasia in the anal transitional zone; (2) the Anoscopist noticed that there is remodeling of the anal canal epithelium, replacing thickened dysplastic epithelium with thin, translucent epithelium, which is normal.

An exemplar protocol includes the following steps (Table 1). (1) Begin with an IM injection of Gardasil-9 to prime subsequent immunizations. (2) Concurrent with (1), begin intra-anal applications of 5% imiquimod on MWF (Monday-Wednesday-Friday) schedule. (3) At weeks 3, 6, 9 and 12, administer perianal immunizations. (4) Continue thrice weekly imiquimod intra-anal applications through week 20. (5) Anal cytology, HPV DNA assay and high resolution anoscopy (HRA) at weeks 0, 3, 6, 9, 12, 16, 20, 24, 32, 40, 48, 60, 72, 84, and 96.

TABLE 1

Exemplar Schedule

| Time | Vaccine | Location | imiquimod |
|---|---|---|---|
| Wk 0 | Gardasil | Deltoid | Start 3×/wk |
| Wk 3 | Gardasil | Perianal | 3×/wk |
| Wk 6 | Gardasil | Perianal | 3×/wk |
| Wk 9 | Gardasil | Perianal | 3×/wk |
| Wk 12 | Gardasil | Perianal | 3×/wk |
| Wk 16 | — | — | 3×/wk |
| Wk 20 | — | — | Discontinue |
| Wk 24 | — | — | Discontinue |
| ... | ... | ... | ... |
| Wk 48 | | | End of Study |

Example 2 Therapeutic Perianal Immunizations with GARDASIL-9 and Concurrent Imiquimod: Treating HPV Infection and Anal Intraepithelial Neoplasia (AIN) in HIV-Negative and HIV-Positive Patients This non-limiting example describes a novel approach to treatment with intra-anal imiquimod used in conjunction with perianal immunizations with the nonavalent HPV (nHPV) vaccine. This innovative immunologic approach to treat anal HPV infection and dysplasia can be accomplished with much less morbidity and may generate an HPV specific immune response, lessening the likelihood of the emergence of dysplasia due to either reactivation or reinfection with oncogenic strains of HPV.

Patients receive an intramuscular immunization of nHPV followed by 4 perianal (mucosal) immunizations. Concurrently, patients apply thrice weekly mucosal applications of imiquimod. Lesion size and morphology are monitored by serial high-resolution anoscopies. The treatment can eliminate HPV DNA, followed by the regression of anal intraepithelial neoplasia (AIN).

Serial mucosal biopsies and blood samples are collected before, during and after the twenty week treatment period to assess the development and augmentation of anti-HPV cellular and humoral responses. To that end, flow cytometry and ELISA are combined to measure the HPV-specific cellular responses, antibody titers and dendritic cell activation. Without wishing to be bound by any particular theory, imiquimod may recruit plasmacytoid cells to the vaccination site and in that manner activate HPV-specific immune responses. Without wishing to be bound by any particular theory, the treatment could lead to long-lasting immunity to HPV and protection against recurrent anal dysplasia.

This approach is innovative in the use of intra-anal imiquimod in conjunction with perianal immunizations with nHPV vaccine and could result in the regression of AIN and loss of HPV DNA. Additionally, this could reduce reactivation of latent HPV DNA and acquisition of novel types of oncogenic HPV types through the generation of HPV specific cellular and humoral responses.

Example 3 HIV Positive Patient with Moderate Immunosuppression and Recurrent High Grade Anal Dysplasia Post Several Ablative Treatments Who has been Treated with Intra-Anal Imiquimod Cream and Concurrent HPV-9 Vaccinations Followed by Treatment with Intra-Anal 5-Fluorouracil Cream Case Report Summary: The patient is a 60 year old HIV positive gay white male with chronic HIV infection who presents with recurrent high grade squamous intraepithelial lesion (HSIL) post multiple ablative treatments. The patient received treatment for his HIV disease with a combination of anti-retroviral medicatons (abacavir, etravirine, prezista and ritonavir which was later modified to dolutegravir, etravirine and prezista and ritonavir). Over the past two years the CD4 count has been in the range of 250-350 and there has been low level HIV viremia (40-400 copies range per ml of plasma) due to intermittent adherence. The patient has other co-morbid conditions including hepatitis C, hypertension, hyperlipidemia, osteoporosis, and high risk sexual activity.

The patient has the following history of the diagnosis and treatment of high grade anal dysplasia:

Oct. 13, 2013 Anal pap smear-low grade squamous intraepithelial lesion (LSIL)

Dec. 26, 2013 High resolution anoscopy (HRA) with biopsies at 2 and 12 o'clock positions both specimens are anal intraepithelial lesions grade 1 (AIN 1). Anal pap-LGSIL and HPV typing showed other high risk types as well as low risk types.

Apr. 22, 2014 HRA with AIN 3 on biopsy at the 8 o'clock position. Patient was referred to a colorectal surgeon.

Aug. 19, 2014 Colorectal surgeon biopsied and treated HSIL (high grade squamous intraepithelial lesion) at 8 and 10 o'clock with CO2 laser fulguration. LSIL identified at 3 o'clock and this was treated with $CO_2$ laser fulguration also.

Dec. 4, 2014 HRA with biopsies: 4 o'clock—AIN 2; 9 o'clock—AIN 3; 10 o'clock—AIN 3; 12 o'clock—AIN 1.

Dec. 14, 2014 HRA with hyfrecation of HSIL.

Jan. 19, 2015 Colorectal surgeon visit for pain and bleeding per anus. Examination revealed anal fissure (possible complication from previous colorectal surgery).

Jan. 20, 2015 Begins treatment for hepatitis C, genotype 1 with 12 weeks of sofosbuvir/ledipasvir with sustained virologic response 12 weeks post completion of therapy.

Apr. 15, 2015 HRA with anal pap showing HSIL and biopsies as follows: 4 o'clock—AIN 3; 4 o'clock distal tail of lesion—AIN 1; 8 o'clock—AIN 2; 10 o'clock—AIN 1; 12 o'clock—AIN 1.

May 12, 2015 Patient referred to colorectal surgeon who recommended HRA with biopsies and fulguration, but the patient refused further operative procedures.

May 29, 2015 Discussed immunotherapy for recurrent HSIL after failing ablative therapies described above. Patient received HPV-9 vaccine intramuscular in the deltoid. This is the start of the immunotherapy protocol. Patient starts the intra-anal application of 5% imiquimod cream three times per week.

Aug. 7, 2015 HRA done and biopsies taken. Results of biopsies: 3 o'clock—AIN 2; 4 o'clock—AIN 1; 9 o'clock—AIN 1; 10 o'clock distal—AIN 1; 12 o'clock AIN 2. HPV typing positive for other high risk types. Patient complains of anal irritation and spotting of blood per anus due to the imiquimod cream treatments. Pt told to wait until irritation has abated before continuing the imiquimod cream treatments. First perianal HPV-9 vaccination given.

Sep. 30, 2015 HRA done and biopsies taken. Results of biopsies: 3 o'clock—AIN 1; 4 o'clock—AIN 1; 9 o'clock—AIN 1; 10 o'clock—AIN 1; 12 o'clock—benign. Anal pap showed LSIL and correlates well with the biopsy results. HPV assay shows continued presence of other HPV high risk types. Second perianal HPV-9 vaccination given.

Oct. 28, 2015 HRA with biopsies taken. Results of biopsies: 1 o'clock—AIN 1; 4 o'clock—benign; 9 o'clock—AIN 1; 12 o'clock—AIN 1. Anal pap showed atypical cells of undetermined significance (ASCUS). $3^{rd}$ perianal HPV-9 vaccination given.

Dec. 9, 2015 HRA done with biopsies. Results of biopsies: 3 o'clock AIN—1; 6 o'clock—AIN 1; 9 o'clock—benign.

Jan. 15, 2016 $4^{th}$ perianal HPV-9 vaccination given. Discontinue 5% intra-anal imiquimod cream and begin 5% 5-fluorouracil cream intra-anally three times a week for 20 weeks.

Apr. 19, 2016 Patient is using 5-fluorouracil cream intra-anally two times a week and was encouraged to use this cream three times a week.

Apr. 21, 2016 HRA with biopsies. Results of biopsies: 3 o'clock—AIN 1; 5 o'clock—AIN 1; 6 o'clock—AIN 1; 9 o'clock—AIN 1; 10 o'clock—benign; 12 o'clock—benign.

Jun. 20, 2016 HRA with biopsies. Results of biopsies: 3 o'clock—benign; 9 o'clock—benign anal mucosa; 10 o'clock—benign anal mucosa; 12 o'clock—benign anal mucosa. Anal pap-negative for intraepithelial lesion and malignancy and the transformation zone is present.

The above case report represents a case of recurrent anal HSIL status post multiple ablative procedures. The patient has HIV infection and thus is moderately immunosuppressed. In spite of the immunosuppression, the patient was able to clear not only HSIL (AIN 2 and AIN 3) but also was able to clear LSIL (AIN 1). The presence of a normal anal pap smear result on Jun. 20, 2016 suggests that in fact the anal dysplasia has resolved and correlates well with the multiple benign anal mucosa biopsy results form Jun. 20, 2016. In this case the immunotherapy protocol (5% imiquimod cream in conjunction with perianal HPV-9 immunizations followed by 4-5 months of 2-3 times weekly intra-anal 5% 5 fluorouracil cream), resulted in clearance of anal dysplasia (AIN 1, AIN 2 and AIN 3). It is presumed that the use of the 5-fluorouracil cream treated nests of dysplastic cells that if not treated would likely lead to recurrent LSIL or HSIL. Thus, the immunotherapy protocol may be useful for patients in a salvage situation who have failed multiple ablative procedures with recurrent HSIL in the setting of immunosuppression due to HIV infection. The results indicate a treatment for HIV positive men who have sex with men (MSM) with recurrent anal HSIL without the possible complications of anal fissures or strictures associated with ablative procedures. The most notable side effects of the immunotherapy protocol was anal and perianal irritation secondary to the use of the 5% imiquimod cream and the 5% 5-fluorouracil cream. Brief cessation of the use of either cream with healing of the anal canal and perianal region or reduction in the frequency of intra-anal treatments resulted in resolution of the irritation, friability and bleeding. Local infusion of 1% lidocaine prior to the perianal vaccinations with HPV-9 resulted in much less burning at the site of HPV vaccination. Additionally, the patient continued to have the presence of HPV other high risk types in the anal canal in spite of HPV vaccinations. This might be due to the immunosuppression secondary to chronic HIV infection.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for treating a human papillomavirus (HPV)-associated neoplasia or a HPV-associated cancer in a subject, comprising:
    providing an immune response modifier and a human papillomavirus (HPV) vaccine;
    administering a first dose of the immune response modifier intra-anally, perianally, or intratumorally;
    administering a first dose the HPV vaccine to the subject;
    continuing to administer one or more doses of the immune response modifier intra-anally, perianally, or intratumorally; and
    administering one or more subsequent doses of the HPV vaccine perianally to the subject, thereby treating the HPV-associated neoplasia or a HPV-associated cancer in the subject,
    wherein the HPV-associated neoplasia or a HPV-associated cancer is selected from the group consisting of anal intraepithelial neoplasia, anal high-grade squamous intraepithelial neoplasia, anal dysplasia, anal cancer, anal tumor and combinations thereof.

2. The method of claim 1, wherein the subject is a human.

3. The method of claim 1, wherein the subject is a male human.

4. The method of claim 1, wherein the subject is a female human.

5. The method of claim 1, wherein the immune response modifier and the HPV vaccine are provided in one composition.

6. The method of claim 1, wherein the immune response modifier and the HPV vaccine are provided in separate compositions.

7. The method of claim 1, wherein the immune response modifier and the HPV vaccine are administered concurrently, sequentially, or alternatively.

8. The method of claim 1, wherein the immune response modifier and the HPV vaccine are administered according to different schedules.

9. The method of claim 1, wherein the immune response modifier is administered before, during or after administering the HPV vaccine.

10. The method of claim 1, wherein the immune response modifier is an immunostimulant.

11. The method of claim 1, wherein the immune response modifier is a local immunostimulant.

12. The method of claim 1, wherein the immune response modifier is a toll-like receptor 7 (TLR7) agonist.

13. The method of claim 1, wherein the immune response modifier is selected from the group consisting of: imiquimod, resiquimod, ANA975 (Isotorabine), ANA773, IPH-32XX, R848, CL097, 852A, CROI2015, GS-9620, PF-4878691, PF-4878691, and a combination thereof.

14. The method of claim 1, wherein the immune response modifier is administered intra-anally.

15. The method of claim 1, wherein the immune response modifier is administered at a dose of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg.

16. The method of claim 1, wherein the immune response modifier is administered at a dose of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$.

17. The method of claim 1, wherein the immune response modifier is administered at about 1-10, 10-20, 20-30, 30-40, 40-50, 50-60, 60-70, 70-80, 80-90, or 90-100 mg per dose.

18. The method of claim 1, wherein the immune response modifier is administered about 1-3 times per day, 1-7 times per week, 1-9 times per month, or 1-12 times per year.

19. The method of claim 1, wherein the immune response modifier is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

20. The method of claim 1, wherein the HPV vaccine is a nonavalent HPV vaccine, bivalent HPV vaccine, quadrivalent HPV vaccine, or a combination thereof.

21. The method of claim 1, wherein the HPV vaccine is GARDASIL, GARDASIL 4, GARDASIL 9, or CERVARIX, or a combination thereof.

22. The method of claim 1, wherein the HPV vaccine is a vaccine protective against HPV 6, 11, 40, 42, 43, 44, 53, 54, 61, 72, 73, 81, 16, 18, 31, 33, 35, 39, 45, 51, 52, 56, 58, 59, or 68, or a combination thereof.

23. The method of claim 1, wherein the HPV vaccine is administered intramuscularly, or perianally, or a combination thereof.

24. The method of claim 1, wherein the HPV vaccine is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg.

25. The method of claim 1, wherein the HPV vaccine is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$.

26. The method of claim 1, wherein the HPV vaccine is administered about 1-3 times per day, 1-7 times per week, 1-9 times per month, or 1-12 times per year.

27. The method of claim 1, wherein the HPV vaccine is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

28. The method of claim 1, wherein a first dose of the immune response modifier and the first dose of the HPV vaccine are administered concurrently.

29. The method of claim 1, wherein the immune response modifier is administered intra-anally.

30. The method of claim 1, wherein the immune response modifier is administered once every about two days.

31. The method of claim 1, wherein the immune response modifier is administered about three times per week.

32. The method of claim 1, wherein the first dose of the HPV vaccine is administered intramuscularly.

33. The method of claim 32, wherein a second dose of the HPV vaccine is administered perianally.

34. The method of claim 1, wherein the HPV vaccine is administered once every about three weeks.

35. The method of claim 1, wherein the immune response modifier and the HPV vaccine are administered for about 1-5, 5-10, 10-15, 15-20, 20-25, 25-30, 30-35, 35-40, 40-45, or 45-50 weeks.

36. A method for treating a human papillomavirus (HPV)-associated neoplasia or a HPV-associated cancer in a subject, comprising:
administering an immune response modifier intra-anally, perianally, or intratumorally about three times a week;
administering a first dose a HPV vaccine intramuscularly to the subject following a first dose of the immune response modifier;
administering one or more subsequent doses of the HPV vaccine perianally to the subject about every 3 weeks, thereby treating the HPV-associated neoplasia or a HPV-associated cancer in the subject,
wherein the HPV-associated neoplasia or a HPV-associated cancer is selected from the group consisting of anal intraepithelial neoplasia, anal high-grade squamous intraepithelial neoplasia, anal dysplasia, anal cancer, anal tumor and combinations thereof.

* * * * *